(12) United States Patent
Berger

(10) Patent No.: US 6,638,210 B2
(45) Date of Patent: Oct. 28, 2003

(54) SURGICAL APPARATUS AND METHODS FOR DELIVERY OF A SLING IN THE TREATMENT OF FEMALE URINARY INCONTINENCE

(75) Inventor: Yitzhak Berger, South Orange, NJ (US)

(73) Assignee: Ethicon, Inc., Somerville, NJ (US)

( * ) Notice: Subject to any disclaimer, the term of this patent is extended or adjusted under 35 U.S.C. 154(b) by 40 days.

(21) Appl. No.: 09/963,355

(22) Filed: Sep. 26, 2001

(65) Prior Publication Data

US 2002/0091373 A1 Jul. 11, 2002

Related U.S. Application Data

(60) Provisional application No. 60/235,438, filed on Sep. 26, 2000.

(51) Int. Cl.[7] ............................................... A61B 17/00
(52) U.S. Cl. ........................................................ 600/30
(58) Field of Search ............................ 600/29–31, 37; 128/DIG. 25, 897, 898; 604/272–274, 263; 606/139, 144, 148, 145, 151

(56) References Cited

U.S. PATENT DOCUMENTS

| 5,013,292 A | | 5/1991 | Lemay |
| 5,112,344 A | | 5/1992 | Petros |
| 5,816,258 A | * | 10/1998 | Jervis .......................... 128/898 |
| 5,899,909 A | * | 5/1999 | Claren et al. ................ 606/119 |
| 5,934,283 A | | 8/1999 | Willem et al. |
| 6,010,447 A | * | 1/2000 | Kardjian ....................... 600/29 |

* cited by examiner

*Primary Examiner*—Samuel G. Gilbert
(74) *Attorney, Agent, or Firm*—Gottlieb, Rackman & Reisman, P.C.

(57) ABSTRACT

Surgical apparatus for treating female stress urinary incontinence include a pair of curved delivery needles, each defining a distal end and a proximal end and adopted to be inserted into the abdomen of a female and to be positioned on either side of the bladder neck so as to define a delivery path for a tape which may be removably attached to the proximal ends of the delivery needles through the vagina for implantation into the abdomen to provide support for the urethra. A pair of curved delivery sheaths, each adapted to be inserted into the abdomen around one of the delivery needles, allow withdrawal of the delivery needles from the abdomen such that the tape is conducted along the delivery path. In the preferred embodiment, the delivery needles also allow simultaneous introduction of a local anesthetic into the abdominal tissues. Methods for treatment of stress urinary incontinence utilizing the surgical apparatus are also disclosed.

30 Claims, 8 Drawing Sheets

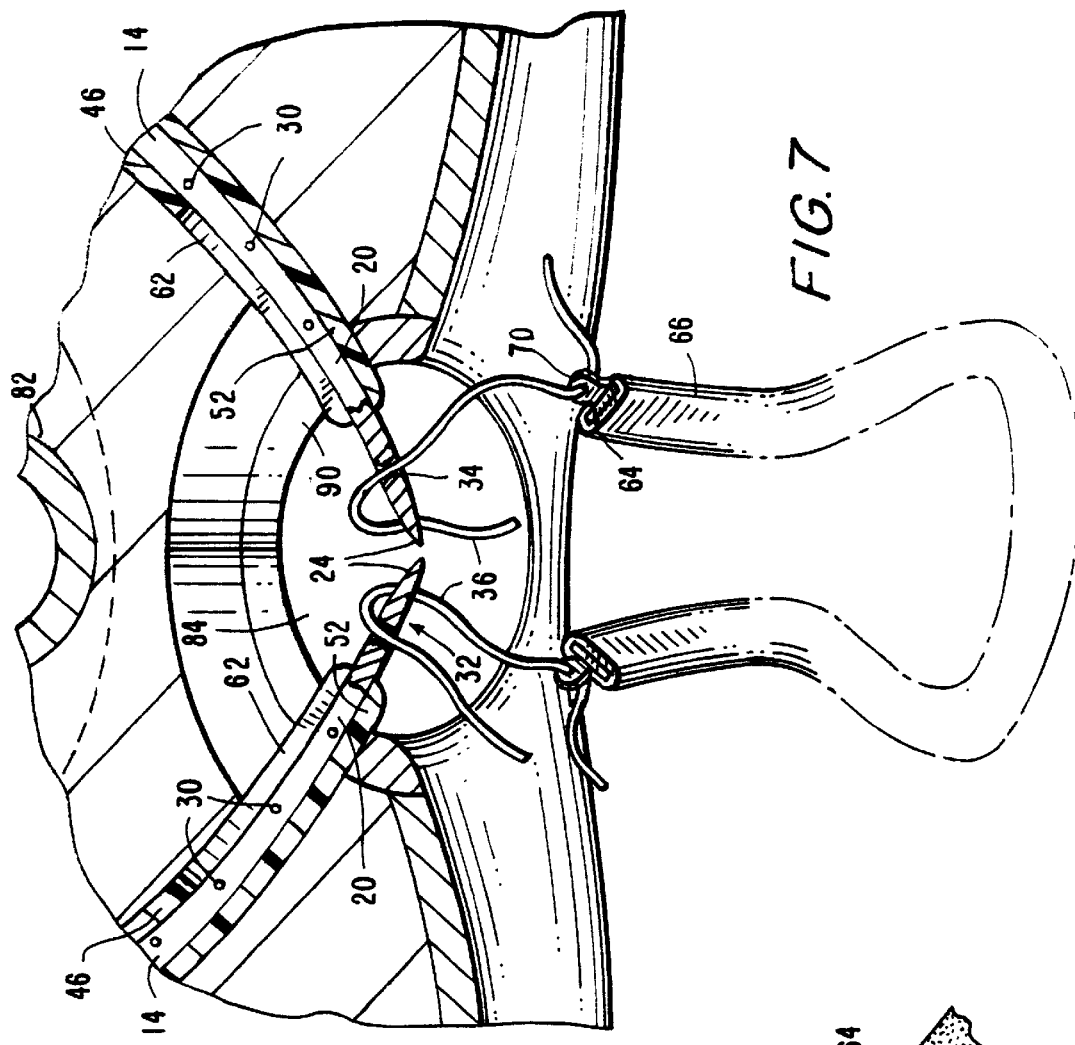
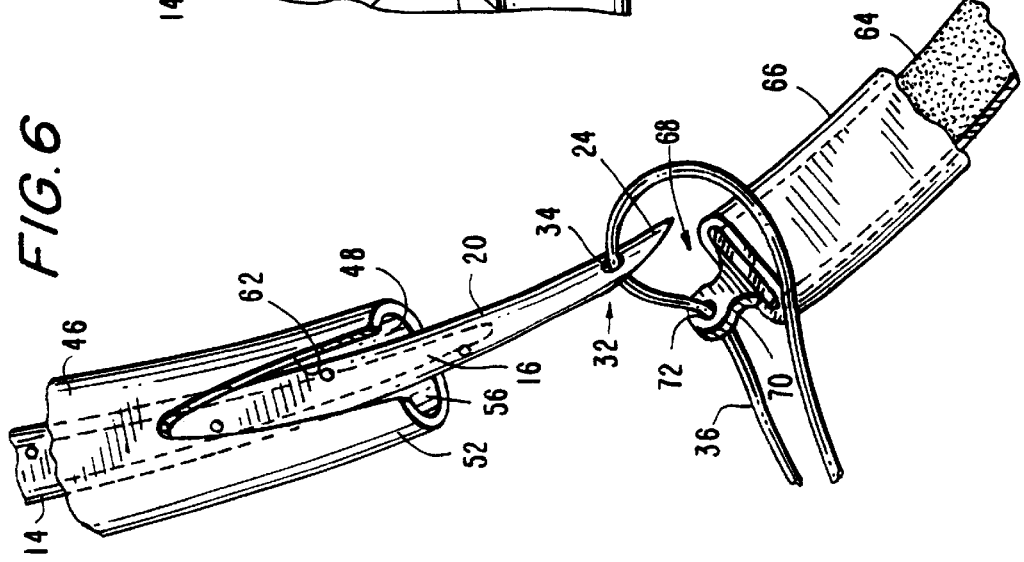

SURGICAL APPARATUS AND METHODS FOR DELIVERY OF A SLING IN THE TREATMENT OF FEMALE URINARY INCONTINENCE

REFERENCE TO RELATED APPLICATIONS

This application claims the benefit of prior copending U.S. Provisional Patent Application Ser. No. 60/235,438, filed Sep. 26, 2000.

TECHNICAL FIELD

The present invention relates broadly to the field of human health care, and in particular, to the treatment of a certain type of urinary incontinence in human beings. More specifically, this invention relates to surgical apparatus and methods for treating stress urinary incontinence in human females.

BACKGROUND OF THE INVENTION

Many women suffer from leakage of urine when they cough, laugh, sneeze or engage in various types of physical exercise. This condition is called stress urinary incontinence ("SUI") and is related to weakness of the muscles within the pelvis that provide support for the urethra and the bladder neck. SUI may be caused by a functional defect of the tissue or ligaments connecting the vaginal wall with the pelvic muscles and pubic bone. Common contributory factors include repetitive straining of the pelvic muscles, childbirth, loss of pelvic muscle tone, and estrogen loss. Such a defect results in an improperly functioning urethra, but unlike other types of urinary incontinence, SUI is not a problem of the urinary bladder.

Non-operative treatment options for patients with SUI can be attempted, by instructing such patients to perform pelvic exercises, known as Kegel exercises, with the intention of strengthening the supporting muscles. However, when these exercises fail to reverse SUI, surgical repair is advised.

Among the many surgical options for SUI that have been described in the medical literature, the introduction into the abdominal cavity of a pubovaginal "sling" has emerged in the past decade as the most effective. In this surgical procedure, a tape-like material, shaped like a flat ribbon, is passed through pelvic tissue and is positioned around the urethra and the bladder neck, forming a loop located between the urethra and the vaginal wall and thereby creating a supportive "hammock" or sling effect. The tape is extended over the pubis and through the abdominal wall and is tightened, after which the surplus tape is cut and removed, and the tape is left implanted in the patient's abdominal cavity.

The tape provides a structure means for tissue ingrowth and thereby provides a newly created body tissue supporting means for the urethra. When pressure is exerted upon the lower abdomen, such as during a cough or sneeze, the sling provides support to the urethra, allowing it to keep its seal and prevent the unwanted discharge of urine.

Three sources for sling materials are available: autologous fascia (a muscle cover that is obtained from the patient's own body, but at least one additional incision is required in order to retrieve the fascia), cadaveric fascia (a muscle cover obtained from a tissue bank, but which may be associated with infectious and immunological side effects) and non-biological synthetic tapes. By using a synthetic material, there is no need for surgical retrieval of autologous fascia and therefore the surgical time, as well as the resulting pain and recovery time for the patient, are reduced when compared with utilizing autologous fascia, while the safety concerns inherent in using cadaveric fascia are avoided.

Nevertheless, significant post-operative complications have been observed when synthetic materials are used, although such complications have not arisen when a new procedure that was recently developed in Sweden is used. In this procedure, a woven synthetic tape material, fabricated of polypropylene mesh and initially protected with a plastic cover that is subsequently removed, is implanted around the urethra via a small vaginal incision, and is delivered into both sides of the pelvis through two tiny incisions in the lower abdomen. This outpatient surgery is termed Tension free Vaginal Tape ("TVT") and can be accomplished with local anesthesia and intravenous sedation, thus making it very attractive for both patients and surgeons for many reasons, not the least of which is that the tension of the tape can be adjusted by the surgeon based upon feedback provided by the patient.

The main (and perhaps the only) drawback of this TVT procedure is the use of two relatively thick, elongated pointed shafts (known as "trocars") that are introduced seriatim into the pelvis through the vagina in order to deliver the synthetic tape, each end of which is initially attached to one of the trocars. The insertion of these sizeable trocars is inherently a "blind" procedure and it can therefore lead to injuries to pelvic structures, such as the urinary bladder, blood vessels, muscles and nerves. Because of these potential complications, the bladder needs to be emptied by catheter each time the trocars and the synthetic tape are passed inside the pelvis. The catheter is placed in the bladder and the surgeon then inserts a metal guide into the catheter which is used to push the bladder away from the surgical tract within the pelvis where the large trocars used for TVT will pass. This requires repeated catheterizations, with insertions of the guide and eventual removal of both the guide and the catheter. In addition, repeated cystoscopic examinations (insertion of an endoscopic device that visualizes the inside of the bladder) must be performed in order to detect injuries to the bladder (bladder perforations). These repeated maneuvers are cumbersome, and they prolong the surgical time required to perform TVT.

Moreover, despite these precautionary manipulations, bladder perforations and bleeding inside the pelvic area from vascular injuries resulting from the TVT procedure of the prior art have been described in the medical literature. The reports of these complications, and the need for repeated preventive manipulations during the surgery, have led to a desire among surgeons who are performing (or who plan to perform) TVT to simplify and to improve the safety of the delivery system. The present invention is directed to meeting the aforesaid desirable objective, by providing a new delivery system with which TVT can become a simpler and safer procedure.

SUMMARY OF THE INVENTION

The invention overcomes the deficiencies of the prior art and provides for improved apparatus and methods for the treatment of female stress urinary incontinence. The invention provides an improved apparatus in the form of a tape delivery assembly which is preferably disposable after a single use, and which can be used not only to deliver a synthetic mesh tape intended to be implanted within the patient's abdominal cavity and to function as a pubovaginal sling, but also, in a preferred embodiment, to introduce a local anesthetic into the adjacent abdominal tissue at the same time.

The tape delivery assembly includes a pair of curved delivery needles, each of which has a varying diameter, but each of which is narrower than the prior art trocars. In the preferred embodiment, each delivery needle comprises a hollow needle body defining an interior needle body passageway and further defining a proximal end and a distal end, the distal end having an opening therein in fluid communication with the passageway; the needle body further defining a plurality of spaced openings disposed circumferentially around the needle body along substantially its entire length, the plurality of spaced openings also in fluid communication with the needle body passageway. The tape delivery assembly further includes means for removably attaching the proximal end of each delivery needle to separate ends of the tape intended to be implanted within the abdominal cavity. In the preferred embodiment, the tape delivery assembly also includes, for each delivery needle, means connected to the distal end of the needle body for removably attaching the needle body to a source of local anesthetic.

The tape delivery assembly further includes, for each delivery needle, a curved delivery sheath, also of varying diameter, and defining an interior sheath passageway for removably receiving a delivery needle therein, and further defining first and second ends having first and second openings therein, respectively, each opening in communication with the sheath passageway, the first opening allowing the delivery needle to be introduced into the sheath passageway, and the second opening allowing the delivery needle to be withdrawn from the sheath passageway.

In practice, the curved delivery needles are introduced into the patient's abdominal cavity via two small incisions made in the lower abdominal wall, and while (in the preferred embodiment) local anesthetic is continuously introduced through each needle body, the delivery needles are inserted into and through the pelvic tissue such that the needle bodies are ultimately positioned with their proximal ends adjacent one another and extending through the vaginal wall (via an incision previously made therein), and with the adjacent portions of the needle bodies positioned on opposite sides of the bladder neck adjacent the urethra, thereby defining a delivery path for the tape to be implanted in the patient's abdominal cavity. A delivery sheath is then inserted around each delivery needle through the abdominal incision, such that the delivery sheath envelops the delivery needle along substantially its entire length, except for the proximal end thereof, and such that the delivery sheaths are situated along the delivery path defined by the delivery needles.

The tape to be implanted within the patient's abdominal cavity is then introduced via the vagina, and each end of the tape is attached to the proximal end of one of the delivery needles via the attachment means. The delivery needles are then withdrawn from the delivery sheaths, thereby pulling or conducting the tape into the delivery sheaths, and the tape ends are thereafter detached from the delivery needles, leaving the tape disposed along the delivery path within the delivery sheaths. The delivery sheaths are then withdrawn, and the tape remains, already positioned appropriately for completion of the TVT procedure in accordance with the prior art. Thus, the invention also provides an improved method for the treatment of stress urinary incontinence in which the improved apparatus of the invention is utilized.

BRIEF DESCRIPTION OF THE DRAWINGS

These and other aspects, features, objects and advantages of the present invention will become more apparent from the following detailed description of the presently most preferred embodiment thereof (which is given for the purposes of disclosure), when read in conjunction with the accompanying drawings (which form a part of the specification, but which are not to be considered limiting in its scope), wherein:

FIG. 6 is an enlarged plan view depicting the illustrative attachment means of the present invention;

FIG. 7 is a view, partially in cross-section, depicting the manner in which a synthetic tape is introduced into the abdominal cavity through the vagina;

DETAILED DESCRIPTION OF THE PREFERRED EMBODIMENT

Figure 1:
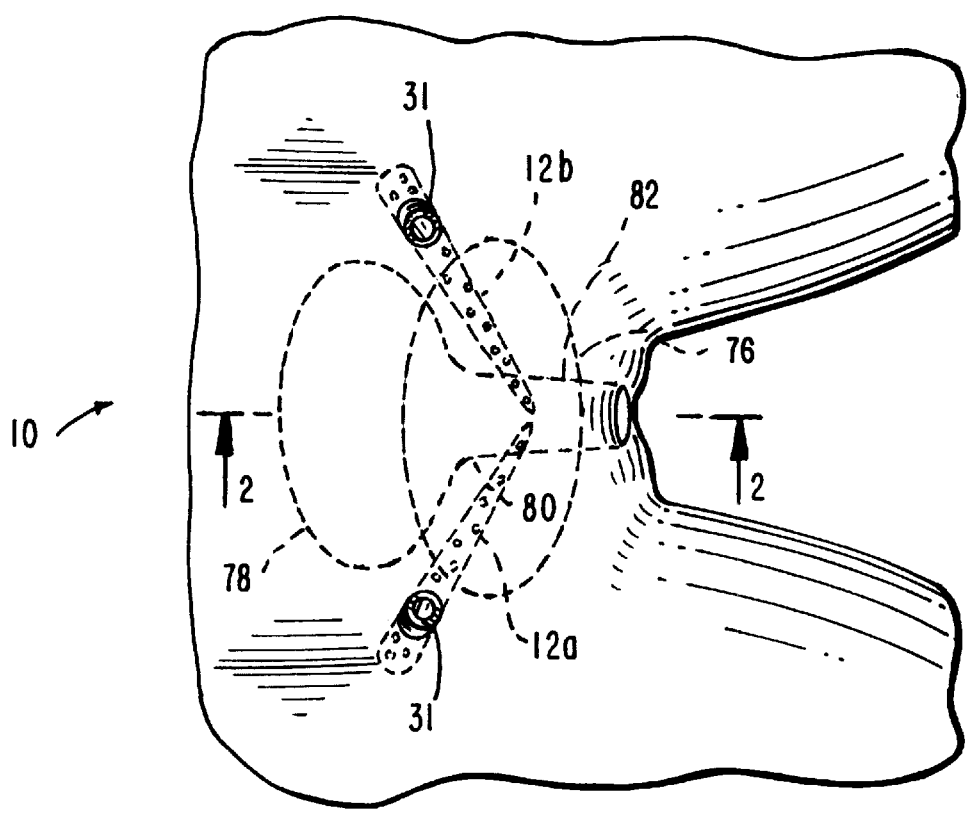
FIG. 1 is a schematic view of the torso of a human female patient, viewed from above, depicting portions of the preferred embodiment of the present invention in place within the abdominal cavity.
Figure 10:
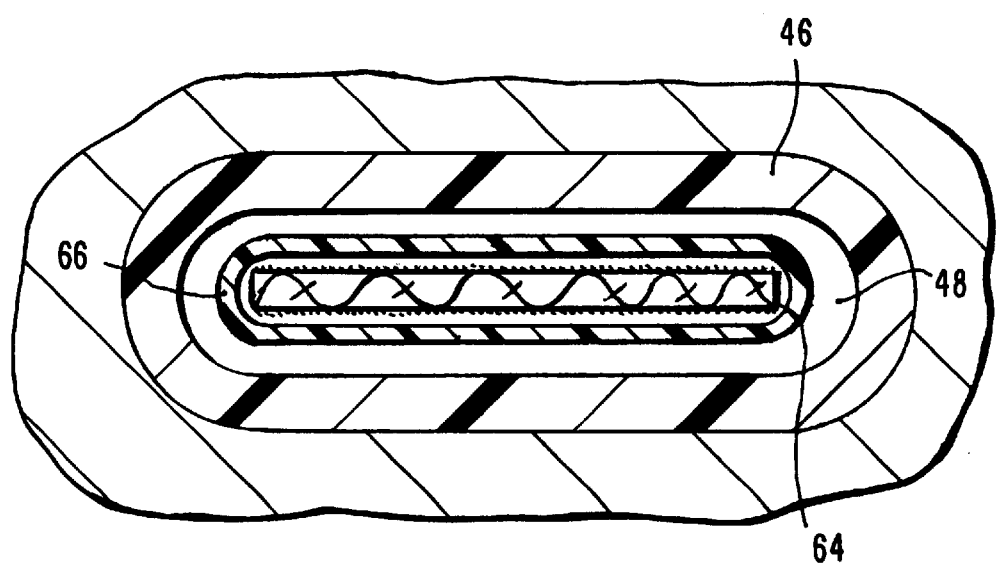
FIG. 10 is an enlarged cross-sectional view, similar to FIG. 5, but taken substantially along the lines 10—10 of FIG. 9.
Figure 2:
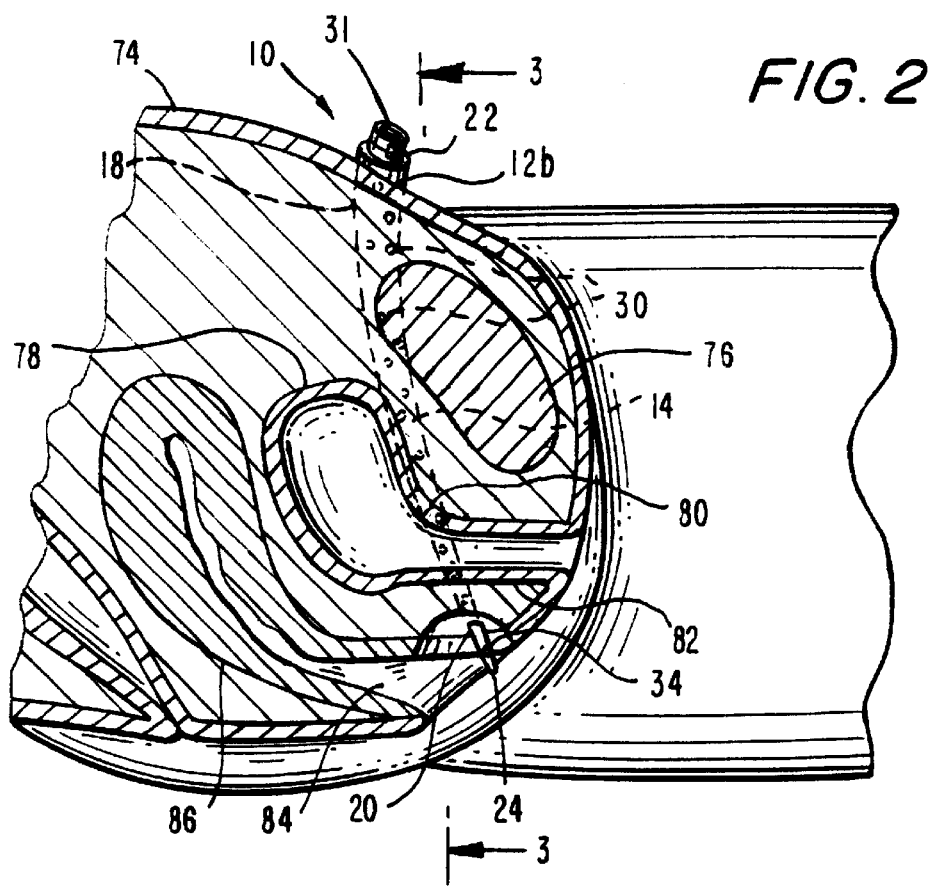
FIG. 2 is an enlarged cross-sectional view, taken substantially along the lines 2—2 of FIG. 1.
Figure 5:
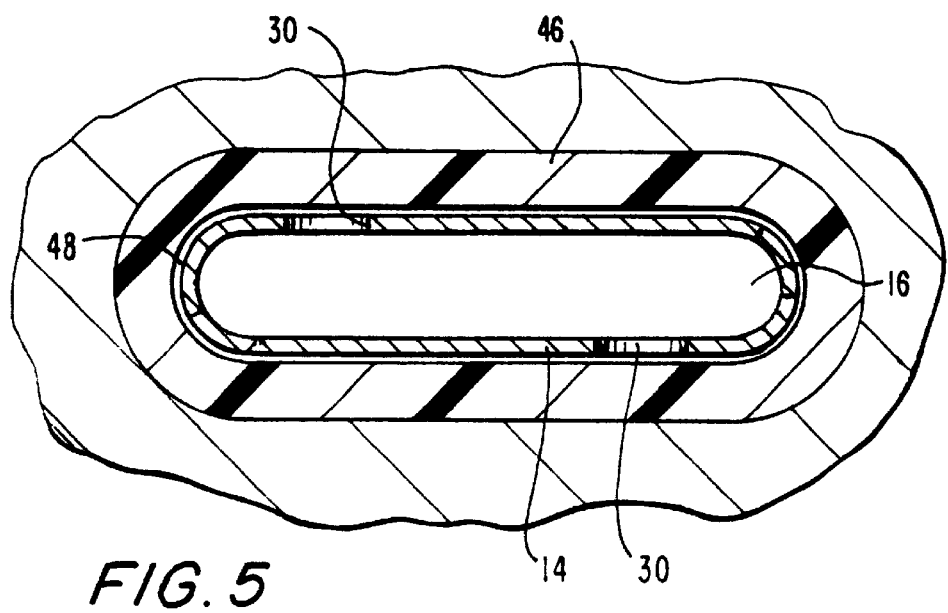
FIG. 5 is a still further enlarged cross-sectional view, taken substantially along lines 5—5 of FIG. 4.

The preferred embodiment of the present invention will now be further described with reference to the accompanying drawings, wherein like reference numerals designate like or corresponding parts throughout the several views. Referring first to FIGS. 1–6, the tape delivery assembly of the present invention is generally designated 10. Assembly 10 includes a pair of elongated, generally tubular, arcuate delivery needles 12a, 12b. Delivery needles 12a, 12b are fabricated from a material that is compatible with the human body, preferably a rigid metal material that is conventionally used for surgical instruments, such as stainless steel, and may be generally smooth, preferably polished, on their exterior to facilitate penetration of soft tissue.

Delivery needles 12a, 12b each comprise a needle body 14 which is generally hollow and which defines an interior needle body passageway 16. Needle body 14 further defines a distal needle end 18 and a proximal needle end 20, the proximal needle end 20 terminating in a needle tip 24, while the distal needle end 18 terminates (in the preferred embodiment) in a distal needle opening 22 that is in fluid communication with the needle body passageway 16. Needle body passageway 16 preferably extends substantially throughout the interior of needle body 14, from distal needle end 18 to proximal needle end 20, but does not extend all the way to needle tip 24, as best shown in FIG. 6. In the preferred embodiment, needle body 14 further defines a plurality of spaced, preferably generally circular, circumferential needle openings 30 disposed along substantially its entire length, each of the circumferential needle openings also being in fluid communication with the needle body passageway 16. In the preferred embodiment, needle body 14 further defines a needle mouth portion 31 adjacent distal needle opening 22 which is shaped to facilitate mating engagement with removable connecting means as hereinafter described.

Figure 3:
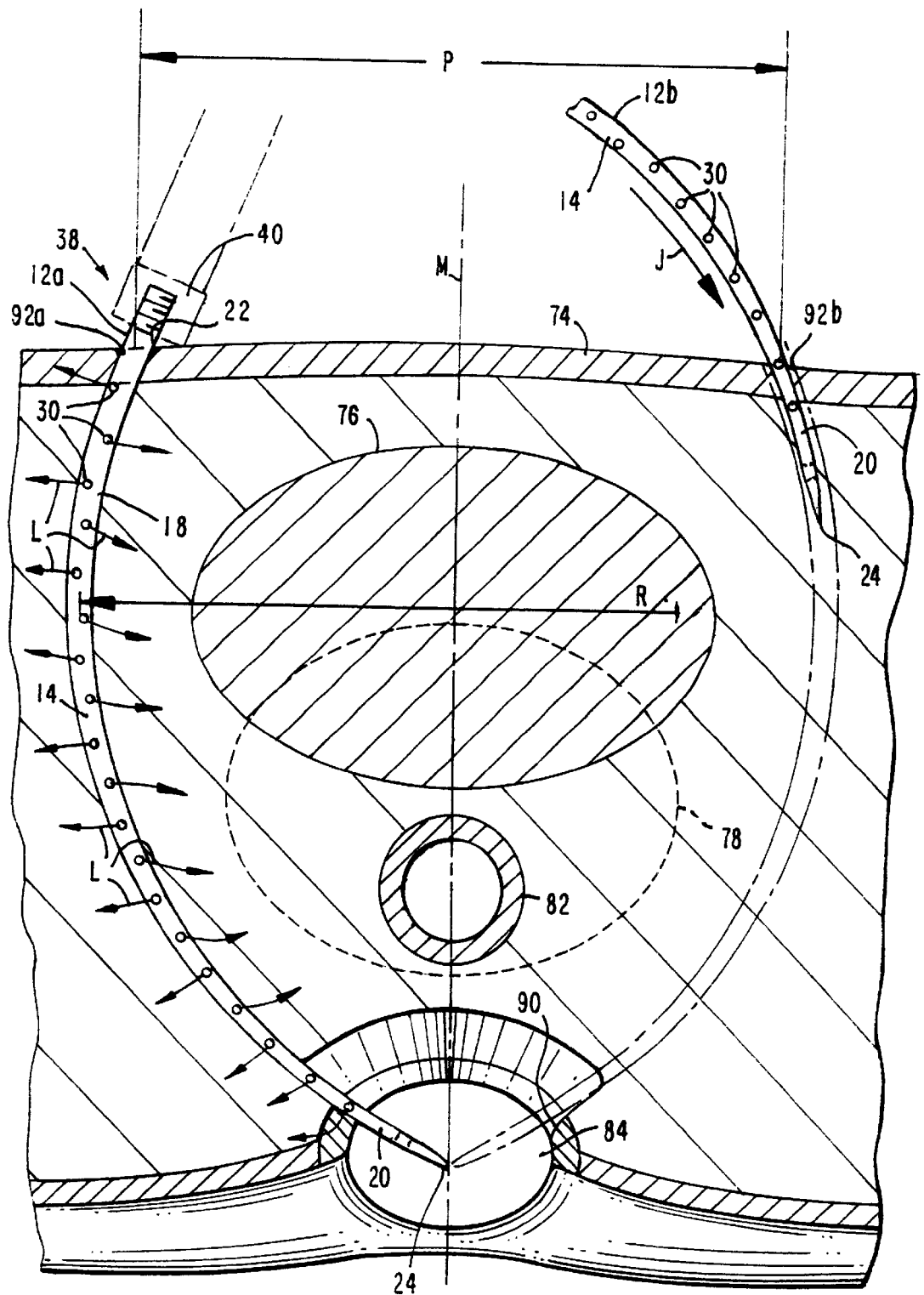
FIG. 3 is a further enlarged cross-sectional view, taken substantially along the lines 3—3 of FIG. 2.
Figure 4:
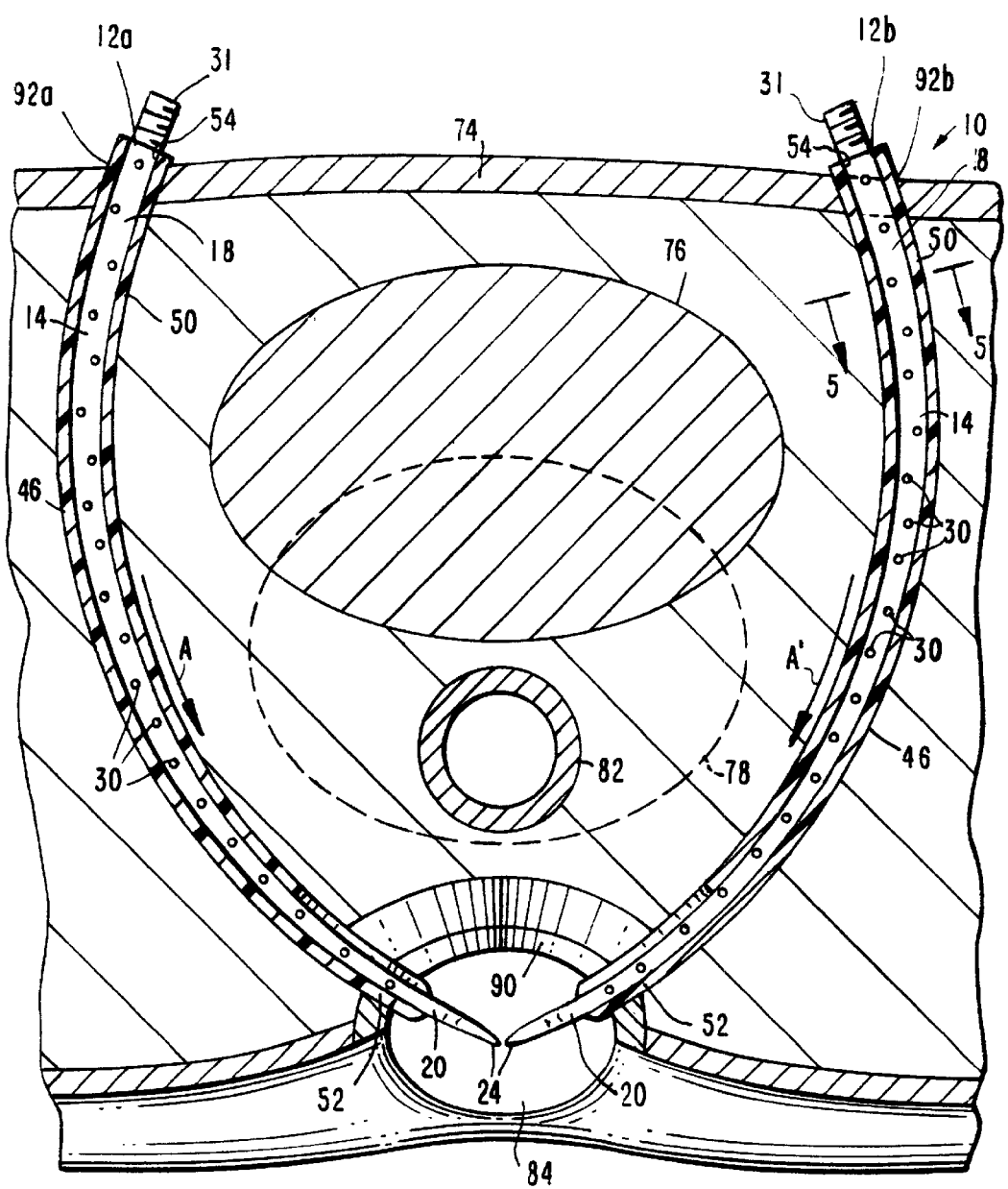
FIG. 4 is a view similar to that of FIG. 3, but showing additional portions of the preferred embodiment of the present invention.

Preferably, needle body 14 is approximately six to seven inches in length, and defines a radius of curvature R that is preferably about 5 in. (as shown in FIG. 3). Needle body 14 is also generally tapered in shape, its diameter transitioning from a larger diameter at distal needle end 18 to a smaller diameter at proximal needle end 20, although it is to be understood that while the term "diameter" is used herein, as shown best in FIG. 5 both needle body 14 and needle body passageway 16 preferably have a cross section which is noncircular, but which is generally oval or ellipsoidal, thus defining a major diameter and a minor diameter. Preferably, the major diameter of needle body 14 at distal needle end 18 is about 0.5 in., while the minor diameter of needle body 14 at distal needle end 18 is preferably about 0.3 in. Preferably, the major diameter of needle body 14 tapers in a substantially continuous manner from about 0.5 in. at distal needle end 18 to about 0.2 in. at proximal needle end 20, with the minor diameter preferably also tapering in a proportional fashion. Needle tip 24 is preferably arrow-shaped, and is adapted to perforate layers of tissue, such as fascia, muscle, fat and skin, in a known manner. Preferably, the thickness of the metal out of which needle body 14 is fabricated is about 0.1 in. throughout, and therefore the major diameter of distal needle opening 22 is preferably about 0.4 in. and the minor diameter of distal needle opening 22 is about 0.2 in. The diameter of each circumferential needle opening is preferably about 0.05 in.

Tape delivery assembly 10 further includes means for removable attachment of each delivery needle 12a, 12b to one end of a tape intended to be implanted within a patient's abdominal cavity. The attachment means comprises means 32, generally disposed at proximal needle end 20 of needle body 14 and adjacent to needle tip 24, for engaging a length of a sterile thread-like material 36 (e.g., conventional surgical suture), and illustratively preferably comprising a needle eyelet 34 adapted to engage the thread-like material, as shown best in FIG. 6.

In the preferred embodiment, tape delivery assembly 10 further includes, for each delivery needle 12a, 12b, means for infusion of a local anesthetic into the abdomen through the delivery needles, although it is to be understood that such infusion means is an optional (albeit desirable) feature of the invention which may be omitted (if, for example, the patient has already been anesthetized via a general or spinal anesthetic) without adversely affecting the tape delivery aspects of the invention. If utilized, the infusion means preferably comprises the aforementioned means for removably connecting the needle body to a source of local anesthetic.

The connecting means 38 is disposed at distal needle end 18 of needle body 14 and is a conventional needle fitting which illustratively preferably comprises a Luer-Lok connector 40, one end of which is adapted for mating engagement with needle mouth 31 adjacent distal needle opening 22, and the other end of which may illustratively be connected to a syringe (not shown) filled with a suitable local anesthetic to an exemplary capacity of ten cubic centimeters (10 cc). Preferably, the local anesthetic that is used is a mixture of any conventional, commercially-available short term local anesthetic and any conventional, commercially-available long term local anesthetic, most preferably an equal parts mixture of a short term local anesthetic such as Lidocaine or Xylocaine and a long term local anesthetic such as Marcaine. Delivery needle 12a is thus configured for infiltration of anesthetic from the syringe through Luer-Lok connector 40 into needle body passageway 16, for ultimate passage through the plurality of circumferential needle openings 30.

Tape delivery assembly 10 further includes, for each delivery needle 12a, 12b, an elongated, tubular, arcuate delivery sheath 46 which is generally hollow and which defines an interior sheath passageway 48. Delivery sheath 46 further defines a distal sheath end 50 and a proximal sheath end 52, terminating in a distal sheath opening 54 and a proximal sheath opening 56, respectively, that are in fluid communication with the sheath passageway 48. Sheath passageway 48 extends throughout the full length of sheath 46, from distal sheath end 50 to proximal sheath end 52. Delivery sheath 46 is fabricated from a material that is compatible with the human body, preferably a flexible material that is conventionally used in surgical procedures, (such as plastic or silicone), and as shown best in FIG. 6, proximal sheath end 52 preferably includes an elongated cutout 62 extending from proximal sheath opening 56 part of the way towards distal sheath end 50, in order to facilitate the introduction into sheath passageway 48 the distal needle end 18 of a delivery needle 12a, in the manner to be described hereinbelow.

Preferably, delivery sheath 46 is also approximately six to seven inches in length, and defines a radius of curvature (not shown) that is also preferably about 5 in. Delivery sheath 46 is also generally tapered in shape, its diameter transitioning from a larger diameter at distal sheath end 50 to a smaller diameter at proximal sheath end 52, although it is to be understood that while the term "diameter" is used herein, as shown best in FIG. 5 both delivery sheath 46 and sheath passageway 48 preferably have a cross section which is non-circular, but which is generally oval or ellipsoidal, thus defining a major diameter and a minor diameter. Preferably, the major diameter of delivery sheath 46 at distal sheath end 52 is about 0.7 in., while the minor diameter of delivery sheath 46 at distal sheath end 52 is preferably about 0.4 in. Preferably, the major diameter of delivery sheath 46 tapers in a continuous manner from about 0.7 in. at distal sheath end 52 to about 0.3 in. at proximal sheath end 54, with the minor diameter preferably also tapering in a proportional fashion, and the thickness of the material out of which delivery sheath 46 is fabricated is preferably about 0.1 in. throughout. Therefore the major diameter of distal sheath opening 54 is preferably about 0.6 in. and the minor diameter of distal sheath opening 54 is about 0.3 in. Notwithstanding the foregoing, however, and for reasons that will become apparent to those skilled in the art, while the shape of delivery sheath 46 is generally similar to the shape of delivery needle 12a, the interior dimensions of delivery sheath 46 are adapted to be slightly larger than the exterior dimensions of delivery needle 12a, so as to enable delivery sheath 46 to surround and envelop delivery needle 12a, in the manner to be described hereinbelow.

Referring now to FIG. 7 in addition to the aforementioned FIGS. 1–6, tape delivery assembly 10 also includes a tape 64 for implantation into a patient's abdominal cavity, which may be fabricated from any appropriate tissue-compatible synthetic material. An exemplary but preferred synthetic material is PROLENE® polypropylene mesh, a mesh having a thickness of 0.7 mm and openings of about 1 mm manufactured by Ethicon, Inc. of Somerville, N.J., U.S.A. This material, which is approved by the U.S. Food and Drug Administration for implantation into the human body, is adapted to adhere to the pelvic tissues adjacent to the bladder neck and urethra, and in its commercial embodiment this material is therefore generally surrounded initially by a removable plastic wrapping or tape covering 66 which prevents the synthetic tape material from adhering prematurely to the pelvic tissues before it has been properly positioned for implantation, after which the covering 66 may be removed.

Tape 64 may be of any convenient shape and size that suits the intended purpose of this invention. Preferably, it is one centimeter (i.e., approximately 0.4 in) wide, with a length of approximately sixteen inches, and the exemplary synthetic material mentioned above is currently available commercially from the source mentioned above with those dimensions, although as far as the length is concerned, it will be apparent to those skilled in the art that, depending upon the size of the patient into whose abdomen it is to be implanted, it may be necessary to cut and trim the tape to an appropriate length, which can be done at the time of implantation.

As shown best in FIG. 6, the attachment means of tape delivery assembly 10 further comprises, at each end of tape covering 66, means 68 for removably receiving sterile thread-like material 36 to enable removable attachment of tape 64 to delivery needles 12a, 12b. Receiving means 68 illustratively preferably comprises a loop-shaped "dog ear" protrusion 70, having a tape eyelet 72 bored therethrough which is adapted to receive thread-like material 36.

The use and operation of tape delivery assembly 10 will now be described with reference to FIGS. 8–11 in addition to the aforementioned FIGS. 1–7. In FIGS. 1–4, 7–9 and 11, the anatomical features of the lower abdominal cavity of a human female patient are depicted, including the abdominal wall 74, the pubic bone 76, the urinary bladder 78, the bladder neck 80, the urethra 82, the vagina 84 and the uterus 86. The method of implanting tape 64 in the patient's abdominal cavity includes the conventional pre-surgical preparatory procedures, including, e.g., prepping and draping the patient, positioning the patient in low lithotomy position in the usual fashion, preparing the local anesthetic mixture described above, and in the preferred embodiment, filling syringes with that mixture and connecting a syringe to the Luer-Lok connector 40 disposed at the distal end of each delivery needle 12a, 12b. Thereafter, the local anesthetic mixture is applied in a conventional manner to the anterior portion 88 of vagina 84, and a longitudinal incision 90, preferably approximately one inch long, is made in the anterior vaginal wall adjacent the bladder neck, at approximately the midpoint of the urethra 82. The urinary bladder 78 is then drained with six inches of 14 Fr. catheter.

The local anesthetic mixture is thereafter applied in a conventional fashion to the skin of the patient's abdominal wall 74 in the suprapubic region, about six centimeters (approximately 2.5 inches) lateral from the midline M on both sides, just above the edge of the pubis, and conventional stab wound incisions 92a, 92b are made therein at those points (see FIG. 3). It is to be understood that stab wound incisions 92a, 92b will be separated by distance P (preferably approximately 5 in.), and that those stab wound incisions 92a, 92b can be made by using delivery needles 12a, 12b themselves, or by using any other appropriate surgical instrument(s). In either case, delivery needles 12a, 12b are inserted into the retropubic space through incisions 92a, 92b, respectively, in the direction shown illustratively by arrow J in FIG. 3, and are then driven lateral to the bladder along the posterior aspect of the pubic bone 76, to such an extent that their proximal needle ends 20 are positioned adjacent to, and on either side of, the bladder neck 80, approximately at the midpoint of the urethra 82, and to such an extent that their needle tips 24 emerge through vaginal wall incision 90, with the needle tips 24 of delivery needles 12a, 12b ultimately located in close proximity to one another within the vagina 84, as shown best in FIGS. 3, 4 and 7.

In accordance with the preferred embodiment of the invention, as the delivery needles 12a, 12b are being inserted and driven into the retropubic space as described above, the local anesthetic mixture is simultaneously ejected from the syringes in a known manner, from whence it passes through the Luer-Lok connectors 40 and into the needle body passageways 16, ultimately being injected into the pelvic tissues adjacent each delivery needle 12a, 12b through the plurality of circumferential needle openings 30, as shown by arrows L in FIG. 3. In addition to anesthetizing the patient, the introduction of local anesthetic in this manner also causes the adjacent pelvic tissues to expand, thereby creating a very narrow circumferential space surrounding each delivery needle, approximately 0.1 in. to 0.2 in. wide, which can be utilized to advantage with the present invention, as described hereinbelow.

After delivery needles 12a, 12b have been inserted into the abdominal cavity and are positioned as described above, it is preferable to perform a cystoscopic examination of the urinary bladder 78 in order to detect any possible perforations of that organ, and if so, to remove and reposition one or both of the delivery needles 12a, 12b. It is to be understood that during the cytoscopic examination, and during any subsequent removal and repositioning of the delivery needles 12a, 12b, additional amounts of the local anesthetic mixture may be introduced via the delivery needle passageways 16 and the circumferential openings 30, as necessary, in the same manner as set forth above.

As soon as the delivery needles 12a, 12b are correctly positioned, the syringes and the Luer-Lok connectors 40 are disconnected from delivery needles 12a, 12b, and the proximal sheath end 52 of a delivery sheath 46 is then positioned within each of incisions 92a, 92b, with the proximal sheath opening 56 of each delivery sheath 46 surrounding the exposed distal needle end 18 of one of the delivery needles 12a, 12b. The delivery sheath 46 is thereafter advanced into the circumferential space surrounding each delivery needle 12a, 12b, in the direction of arrows A, A' (see FIG. 4), such that each delivery needle is ultimately positioned within a sheath passageway 48, and to such an extent that each delivery sheath 46 surrounds and envelops a delivery needle 12a, 12b along substantially its entire length, except for the respective needle tips 24, which remain unsheathed.

The respective ends of tape 64 are then introduced through the vagina 84, and each end is removably tethered to a delivery needle 12a, 12b by connecting engaging means 32 to receiving means 68 via a sufficient length of a thread-like material 36, first by threading the thread-like material through tape eyelet 72 of protrusion 70 on tape covering 66, and then by threading the thread-like material through needle eyelet 34 adjacent needle tip 24 of a delivery needle 12a, 12b. Although each tether thus created may optionally be secured by knotting the thread-like material 36, it will be apparent to those skilled in the art that such knotting will not be necessary to secure the tether if a sufficient length of thread-like material 36 is used.

Figure 8:
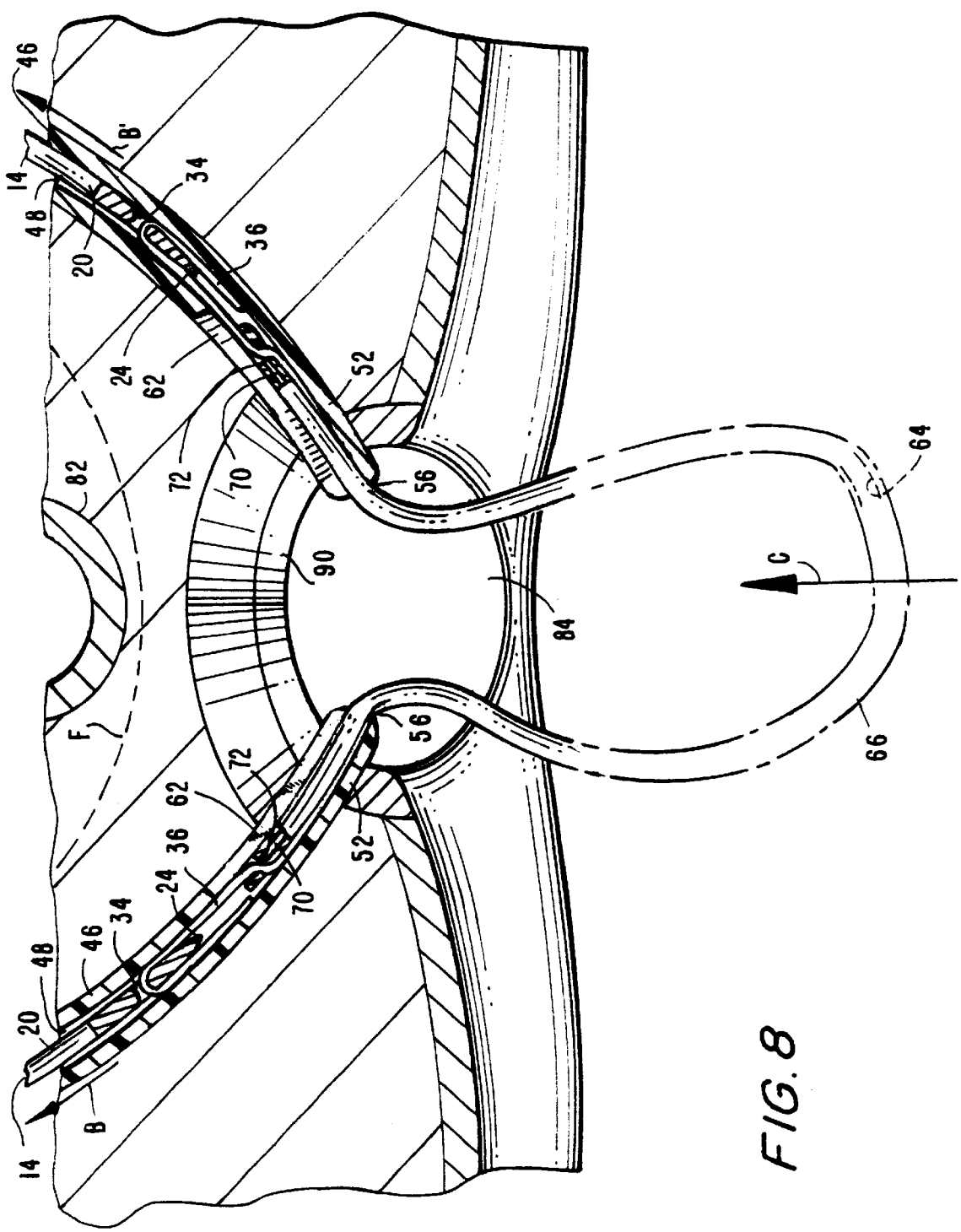
FIG. 8 is a view similar to that of FIG. 7, showing the manner in which the tape is towed into the abdominal cavity in accordance with the present invention.
Figure 9:
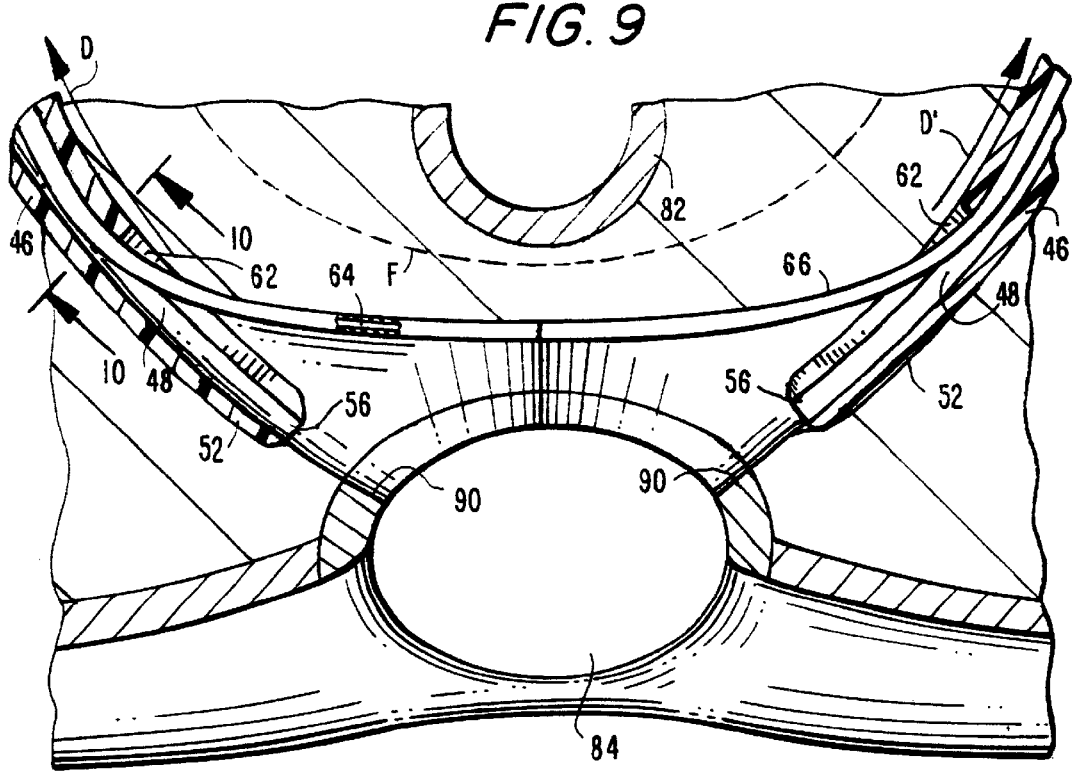
FIG. 9 is a view similar to that of FIG. 8, depicting the tape after it is delivered into the abdominal cavity.
Figure 11:
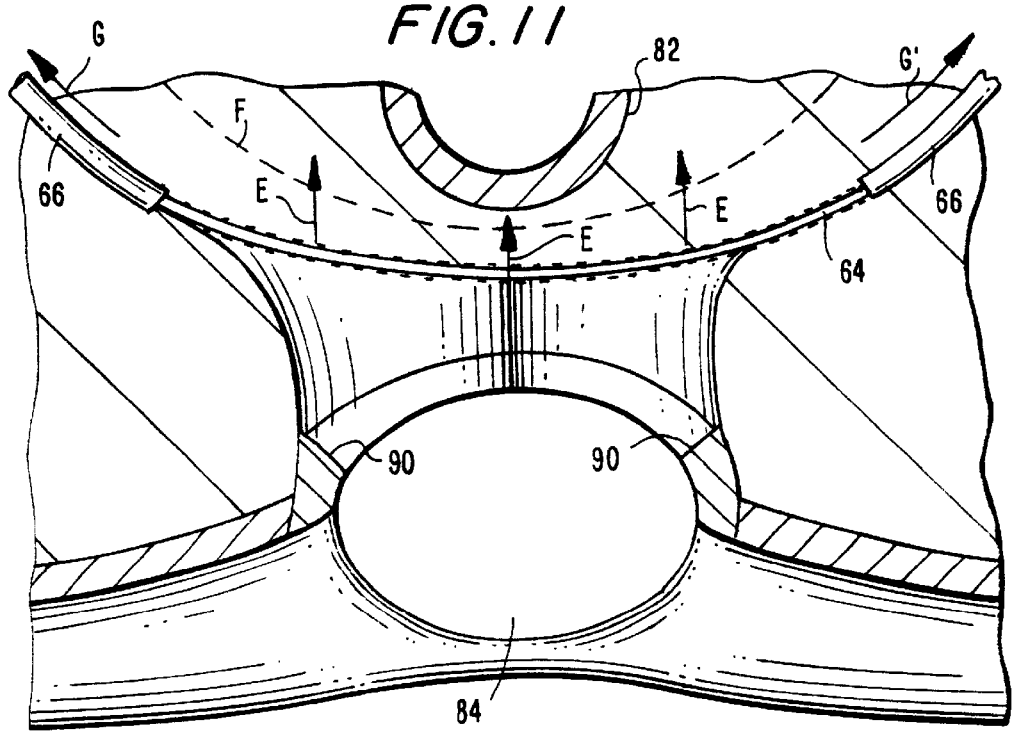
FIG. 11 is a view similar to that of FIG. 9, showing the tape in its final position within the abdominal cavity.

Thereafter, the delivery needles 12a, 12b are slowly withdrawn from the patient's abdominal cavity through delivery sheaths 46 in the direction of arrows B, B' (see FIG. 8), by reversing the motion by which they were driven, and as best shown in FIG. 8, as a result of being tethered to a delivery needle 12a, 12b, one segment of tape 64 is drawn or "towed" into one of the delivery sheaths 46, from proximal sheath end 52 towards distal sheath end 50 in the direction of arrow B, through the entire length of sheath passageway 48, while the other segment of tape 64 is similarly drawn or "towed" into and through the entire length of the other delivery sheath 46 in the direction of arrow B', so that the respective ends of tape 64 thereafter protrude from the patient's abdominal wall 78 (not shown); the portion of the tape 64 outside the vagina is pulled in the direction of arrow C. The delivery needles 12a, 12b are then untethered from the respective ends of the tape 64 by detaching them from the thread-like material 36, and at this point a second cystoscopic examination of the urinary bladder 78 is preferably performed, again in order to detect any possible additional perforations of that organ, and if so, to remove and reposition the tape 64. Thereafter, both delivery sheaths 46 are withdrawn from the patient's abdominal cavity, in the direction of arrows D, D' (see FIG. 9), while tape 64 remains embedded within the pelvic tissue, positioned for completion of the TVT procedure in accordance with the prior art.

Figure 12:
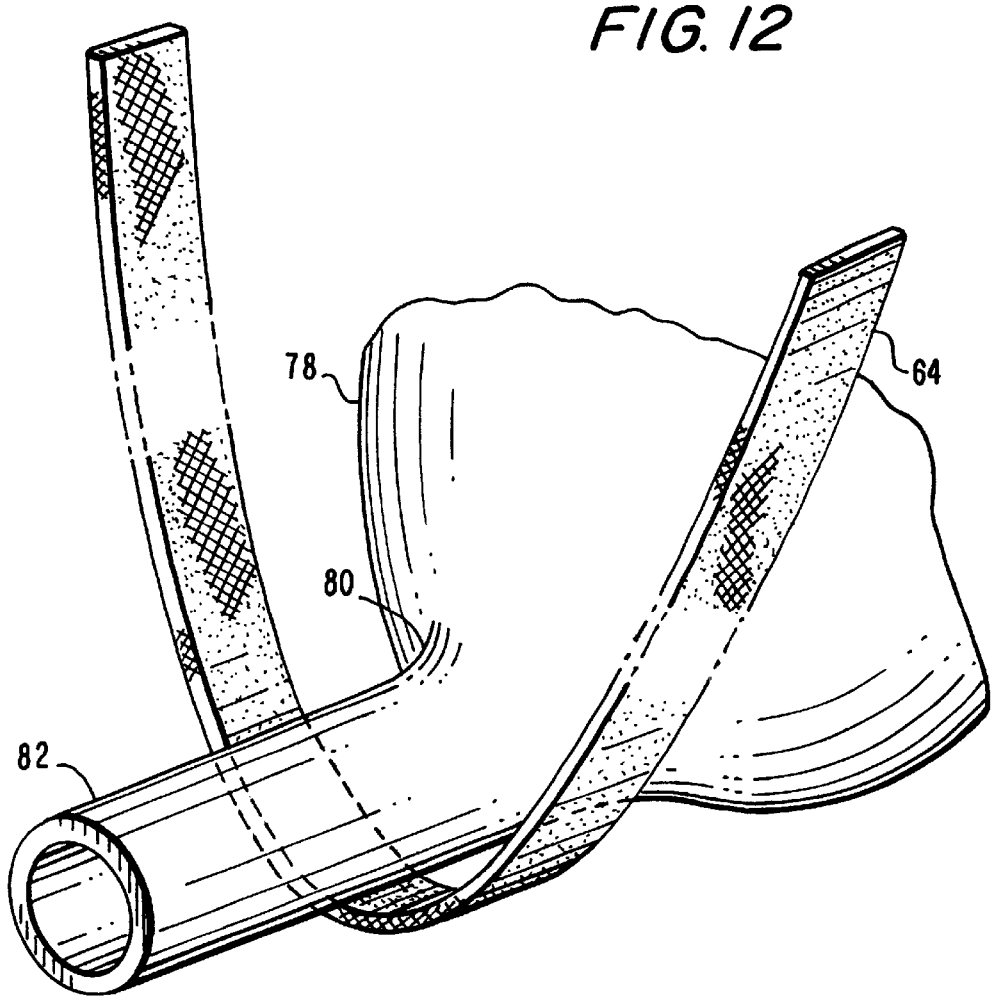
FIG. 12 is a schematic perspective view, also depicting the tape in its final position within the abdominal cavity, where it serves as a pubovaginal sling around the urethra.
Figure 13:
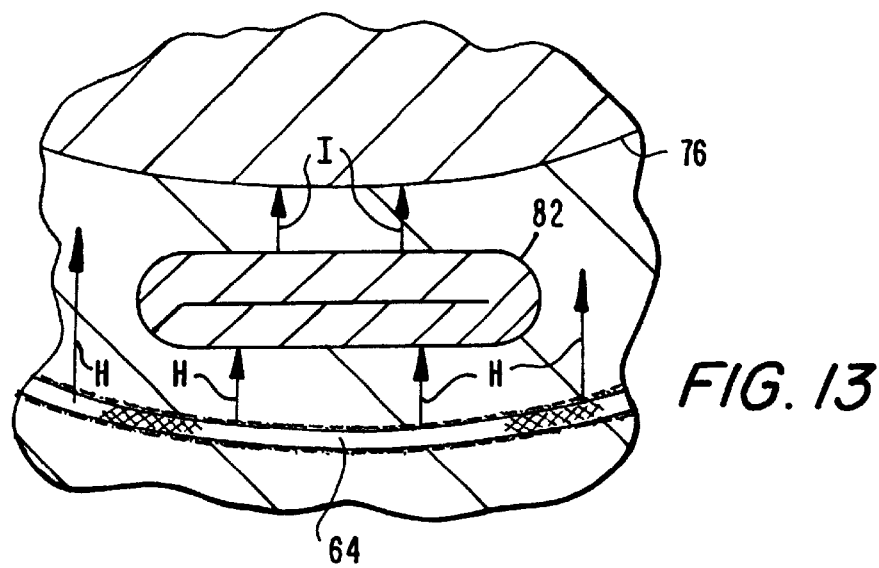
FIG. 13 is a cross-sectional view, illustrating the function of the tape in restoring urinary continence to the patient.

Specifically, using a catheter the urinary bladder 78 is then filled with approximately 250 milliliters of a fluid, typically water, and the patient is requested to cough (not shown). The surgeon is thereby able to determine the operation of the urethra 82 (i.e., to check for leakage), and may adjust the tension of the tape, as necessary, by adjusting the ends of the tape 64 that protrude from the abdominal wall 74, thereby moving the tape 64 in the direction of arrows E (see FIG. 11) and into its final position, as indicated by the dashed lines F in FIGS. 8, 9 and 11. After these adjustments, the tape covering 66 is removed by pulling the sterile thread-like material still attached to the protrusions 70 at the respective ends of tape 64 (not shown), and carrying away the tape covering 66 with them, in the direction of arrows G, G' in FIG. 11. The surplus tape at the abdominal wall is then cut off, and the suprapubic incisions 92a, 92b as well as the vaginal wall incision 90 are closed, leaving tape 64 in the body to form an artificial ligament embedded in the pelvic tissue that provides additional support for the urethra 82, as shown schematically in FIG. 12, in order to restore urinary continence to the patient. The manner in which tape 64 functions, which is well known in the art, is depicted in FIG. 13: when the patient coughs, laughs, or sneezes, etc., the tape 64 assists in the sealing action of the urethra 82, by moving towards the urethra as shown by the arrows H, and urging it toward the pubic bone 76, as shown by the arrows I.

While there has been described what are at present considered to be the preferred embodiments of the present invention, it will be apparent to those skilled in the art that the embodiments described herein are by way of illustration and not of limitation, and that various changes and modifications may be made therein without departing from the true spirit and scope of the present invention, as set forth in the appended claims.

What is claimed is:

1. An assembly for delivery of a tape into the abdomen of a human female through the vagina to serve as a pubovaginal sling in the treatment of stress urinary incontinence, said assembly comprising
   a pair of curved substantially rigid delivery needles adapted for bilateral insertion into the abdomen of a human female for placement on either side of the bladder neck adjacent the urethra, the delivery needles together defining a delivery path for said tape;
   means for removable attachment of each one of said pair of delivery needles to one end of said tape introduced through the vagina; and
   a pair of curved tubular substantially flexible delivery sheaths, each one of said pair of delivery sheaths defining a delivery sheath passageway disposed in the interior thereof and adapted to removably receive one of said pair of delivery needles such that the delivery sheaths are situated along said delivery path,
   whereby each one of said pair of delivery needles may be withdrawn from the abdomen through said delivery sheath passageway and may thereby conduct one end of said tape from the vagina and through said delivery sheath passageway, and thereby position said tape along said delivery path.

2. An assembly according to claim 1, wherein each one of said pair of delivery needles further comprises a distal needle end and a proximal needle end terminating in a needle tip, and wherein said attachment means comprises a thread-like material and means disposed at said proximal needle end adjacent said needle tip for removably engaging said thread-like material.

3. An assembly according to claim 2 wherein said attachment means further comprises means disposed at both ends of said tape for removably receiving said thread-like material.

4. An assembly according to claim 3 wherein said tape is initially provided with a removable covering, and wherein said receiving means is disposed at the respective ends of said covering.

5. An assembly according to claim 4 wherein each one of said pair of delivery sheaths further comprises a distal sheath end terminating in a distal sheath opening in fluid communication with said delivery sheath passageway, and a proximal sheath end terminating in a proximal sheath opening in fluid communication with said delivery sheath passageway, whereby each end of said tape is conducted through one of said delivery sheath passageways from said proximal sheath end towards said distal sheath end.

6. An assembly according to any one of claims 1–5 further comprising means for infusion of a local anesthetic into the abdomen through each one of said pair of delivery needles.

7. An assembly according to claim 6, wherein each one of said pair of delivery needles is hollow and further comprises a needle body defining a needle body passageway disposed in the interior thereof, a distal needle end comprising a distal needle opening in fluid communication with said needle body passageway, and a plurality of spaced circumferential needle openings disposed along substantially the entire length of said needle body, each of said circumferential needle openings also in fluid communication with said needle body passageway, and wherein said infusion means comprises means disposed at said distal needle end of each one of said pair of delivery needles for removably connecting the respective needle bodies to a source of local anesthetic through said distal needle end, such that a charge of local anesthetic may be conveyed into each said needle body from said source of local anesthetic through said needle body passageway and may be discharged into the abdomen from each said needle body through said circumferential needle openings.

8. An assembly according to claim 7 wherein said removable connection means comprises a Luer-Lok connector disposed within said distal needle opening, and wherein said source of local anesthetic comprises a syringe in fluid communication with said Luer-Lok connector and containing a charge of said local anesthetic.

9. An assembly according to claim 8 wherein said local anesthetic comprises a mixture comprising substantially equal parts of a long term local anesthetic and a short term local anesthetic.

10. An assembly for delivery of a tape into the abdomen of a human female through the vagina to serve as a pubovaginal sling in the treatment of stress urinary incontinence, said assembly comprising
- a pair of curved substantially rigid delivery needles adapted for bilateral insertion into the abdomen of a human female for placement on either side of the bladder neck adjacent the urethra, the delivery needles together defining a delivery path for said tape;
- means for removable attachment of each one of said pair of delivery needles to one end of said tape introduced through the vagina;
- means for infusion of a local anesthetic into the abdomen through each one of said pair of delivery needles; and
- a pair of curved tubular substantially flexible delivery sheaths, each one of said pair of delivery sheaths defining a delivery sheath passageway disposed in the interior thereof and adapted to removably receive one of said pair of delivery needles such that the delivery sheaths are situated along said delivery path, whereby each one of said pair of delivery needles may be withdrawn from the abdomen through said delivery sheath passageway and may thereby conduct one end of said tape from the vagina and through said delivery sheath passageway, and thereby position said tape along said delivery path.

11. An assembly according to claim 10 wherein each one of said pair of delivery needles comprises a needle body defining a needle body passageway disposed in the interior thereof, a distal needle end comprising a distal needle opening in fluid communication with said needle body passageway, a proximal needle end terminating in a needle tip, and a plurality of spaced circumferential needle openings disposed along substantially the entire length of said needle body, each of said circumferential needle openings also in fluid communication with said needle body passageway, wherein said attachment means comprises a thread-like material and means disposed at said proximal needle end adjacent said needle tip for removably engaging said thread-like material, and wherein said infusion means comprises means disposed at said distal needle end of each one of said pair of delivery needles for removably connecting the respective needle bodies to a source of local anesthetic through said distal needle end, such that a charge of local anesthetic may be conveyed into each said needle body from said source of local anesthetic through said needle body passageway and may be discharged into the abdomen from each said needle body through said circumferential needle openings.

12. An assembly according to claim 11 wherein said attachment means further comprises means disposed at both ends of said tape for removably receiving said thread-like material.

13. An assembly according to claim 12 wherein said tape is initially provided with a removable covering, and wherein said receiving means is disposed at the respective ends of said covering.

14. An assembly according to claim 13 wherein each one of said pair of delivery sheaths further comprises a distal sheath end terminating in a distal sheath opening in fluid communication with said delivery sheath passageway, and a proximal sheath end terminating in a proximal sheath opening in fluid communication with said delivery sheath passageway, whereby each end of said tape is conducted through said delivery sheath passageway from said proximal sheath end towards said distal sheath end.

15. An assembly according to claim 14 wherein said removable connection means comprises a Luer-Lok connector disposed within said distal needle opening, and wherein said source of local anesthetic comprises a syringe in fluid communication with said Luer-Lok connector and containing a charge of said local anesthetic.

16. An assembly according to claim 15 wherein said local anesthetic comprises a mixture comprising substantially equal parts of a long term local anesthetic and a short term local anesthetic.

17. An assembly for delivery of a tape into the abdomen of a human female through the vagina to serve as a pubovaginal sling in the treatment of stress urinary incontinence, said assembly comprising
- a pair of curved hollow substantially rigid delivery needles adapted for bilateral insertion into the abdomen of a human female for placement on either side of the bladder neck adjacent the urethra, the delivery needles together defining a delivery path for said tape, each one of said pair of delivery needles comprising a needle body defining a needle body passageway disposed in the interior thereof, a distal needle end comprising a distal needle opening in fluid communication with said needle body passageway, a proximal needle end terminating in a needle tip, and a plurality of spaced circumferential needle openings disposed along substantially the entire length of said needle body, each of said circumferential needle openings also in fluid communication with said needle body passageway;
- means for removable attachment of each one of said pair of delivery needles to one end of said tape introduced through the vagina, said attachment means comprising a thread-like material, means disposed at said proximal needle end adjacent said needle tip for removably engaging said thread-like material and means disposed at both ends of said tape for removably receiving said thread-like material;
- means disposed at said distal needle end of each one of said pair of delivery needles for removably connecting the respective needle bodies to a source of local anesthetic through said distal needle end, such that a charge of local anesthetic may be conveyed into each said needle body from said source of local anesthetic through said needle body passageway and may be discharged into the abdomen from each said needle body through said circumferential needle openings; and
- a pair of curved tubular substantially flexible delivery sheaths, each one of said pair of delivery sheaths defining a delivery sheath passageway disposed in the interior thereof, a distal sheath end terminating in a distal sheath opening in fluid communication with said delivery sheath passageway, and a proximal sheath end terminating in a proximal sheath opening in fluid communication with said delivery sheath passageway, each one of said pair of delivery sheaths being adapted to removably receive one of said pair of delivery needles within said delivery sheath passageway such that the delivery sheaths are situated along said delivery path, whereby each one of said pair of delivery needles may be withdrawn from the abdomen through said delivery sheath passageway and may thereby conduct one end of said tape from the vagina and through said delivery sheath passageway from said proximal sheath end towards said distal sheath end, and thereby position said tape along said delivery path.

18. An assembly according to claim 17 wherein said tape is initially provided with a removable covering, and wherein said receiving means is disposed at the respective ends of said covering.

19. An assembly according to claim 18 wherein said removable connection means comprises a Luer-Lok connector disposed within said distal needle opening, and wherein said source of local anesthetic comprises a syringe in fluid communication with said Luer-Lok connector and containing a charge of said local anesthetic.

20. An assembly according to claim 19 wherein said local anesthetic comprises a mixture comprising substantially equal parts of a long term local anesthetic and a short term local anesthetic.

21. A method for treating female stress urinary incontinence comprising the steps of:
providing an apparatus comprising a pair of cured delivery needles, each delivery needle defining a distal needle end and a proximal needle end, a tape for delivery into the abdomen of a human patient to serve as a pubovaginal sling, means for attaching the proximal needle end of each delivery needle to one end of said tape, and a pair of curved tubular delivery sheaths, each delivery sheath defining a delivery sheath passageway disposed therein and adapted to receive therethrough one of said pair of delivery needles;
inserting said delivery needles bilaterally into the abdomen of the patient in the vicinity of the retropubic space and locating said delivery needles on either side of bladder neck adjacent the urethra, such that said delivery needles together define a tape delivery path;
advancing one of said pair of delivery sheaths over each one of said pair of delivery needles such that each one of said pair of delivery needles is received within a delivery sheath passageway and such that said delivery sheaths are situated along said delivery path;
introducing said tape into the body of the patient via the vagina and attaching each respective end of said tape to one of said delivery needles via said attachment means;
withdrawing each one of said pair of delivery needles from the abdomen of the patient through a respective delivery sheath passageway and thereby conducting each end of said tape through a respective delivery sheath such that said tape is positioned along said delivery path on opposite sides of the urethra;
withdrawing each one of said pair of delivery sheaths from the abdomen of the patient; and
leaving said tape implanted in the body thereby to form a pubovaginal sling.

22. A method according to claim 21 further comprising, prior to said insertion step, the step of making a longitudinal incision in the anterior vaginal wall of the patient adjacent the bladder neck at substantially the midpoint of the urethra, and wherein prior to said introducing step, said proximal needle ends extend into the vagina through said anterior wall incision.

23. A method according to claim 22 further comprising, between the two withdrawing steps, the step of detaching each respective end of said tape from a respective one of said pair of delivery needles.

24. A method according to any one of claims 21–23 wherein said apparatus further comprises means for infusion of a local anesthetic into the abdomen of the patient through each one of said pair of delivery needles, and wherein said method further comprises, during said insertion step, the step of infusing a charge of said local anesthetic into the abdomen of the patient through each one of said pair of delivery needles.

25. A method according to claim 24 wherein said tape is initially provided with a removable covering, wherein said attachment means comprises means disposed at the respective ends of said covering for removably attaching each end of said covering to the proximal needle end of each delivery needle, and wherein said method further comprises, prior to said leaving step, the step of removing said covering from said tape.

26. A method for delivery of a tape into the abdomen of a human female patient through the vagina to serve as a pubovaginal sling in the treatment of stress urinary incontinence, said method comprising the steps of
providing an apparatus comprising a pair of curved delivery needles, each delivery needle defining a distal needle end and a proximal needle end, means for attaching the proximal needle end of each delivery needle to one end of said tape, and a pair of curved tubular delivery sheaths, each delivery sheath defining a delivery sheath passageway disposed therein and adapted to receive therethrough one of said pair of delivery needles;
inserting said delivery needles bilaterally into the abdomen of the patient in the vicinity of the retropubic space and locating said delivery needles on either side of bladder neck adjacent the urethra, such that said delivery needles together define a tape delivery path;
advancing one of said pair of delivery sheaths over each one of said pair of delivery needles such that each one of said pair of delivery needles is received within a delivery sheath passageway and such that said delivery sheaths are situated along said delivery path;
introducing said tape into the body of the patient via the vagina and attaching each respective end of said tape to one of said delivery needles via said attachment means;
withdrawing each one of said pair of delivery needles from the abdomen of the patient through a respective delivery sheath passageway and thereby conducting each end of said tape through a respective delivery sheath such that said tape is positioned along said delivery path on opposite sides of the urethra;
detaching each respective end of said tape from a respective one of said pair of delivery needles;
withdrawing each one of said pair of delivery sheaths from the abdomen of the patient; and
leaving said tape implanted in the body thereby to form a pubovaginal sling.

27. A method according to claim 26 further comprising, prior to said insertion step, the step of making a longitudinal incision in the anterior vaginal wall of the patient adjacent the bladder neck at substantially the midpoint of the urethra, and wherein prior to said introducing step, said proximal needle ends extend into the vagina through said anterior wall incision.

28. A method according to claim 27 wherein said apparatus further comprises means for infusion of a local anesthetic into the abdomen of the patient through each one of said pair of delivery needles, and wherein said method further comprises, during said insertion step, the step of infusing a charge of said local anesthetic into the abdomen of the patient through each one of said pair of delivery needles.

29. A method according to claim 28 wherein said tape is initially provided with a removable covering, wherein said attachment means comprises means disposed at the respective ends of said covering for removably attaching each end of said covering to the proximal needle end of each delivery needle, and wherein said method further comprises, prior to said leaving step, the step of removing said covering from said tape.

30. In a method for treatment of stress urinary incontinence, said method comprising the steps of introducing a tape carrying a removable covering into the abdomen of a human female patient through the vagina, positioning said tape on either side of the urethra, removing said cover from said tape and leaving the tape in the body to form a sling around the urethra, the improvement comprising the steps of:

providing an apparatus comprising a pair of curved delivery needles, each delivery needle defining a distal needle end and a proximal needle end, means for attaching the proximal needle end of each delivery needle to one end of said covering, means for infusion of a local anesthetic into the abdomen of the patient through each one of said pair of delivery needles, and a pair of curved tubular delivery sheaths, each delivery sheath defining a delivery sheath passageway disposed therein and adapted to receive therethrough one of said pair of delivery needles;

making a longitudinal incision in the anterior vaginal wall of the patient adjacent the bladder neck at substantially the midpoint of the urethra;

inserting said delivery needles bilaterally into the abdomen of the patient in the vicinity of the retropubic space and locating said delivery needles on either side of bladder neck adjacent the urethra, such that said proximal needle ends extend into the vagina through said anterior wall incision, and such that said delivery needles together define a tape delivery path, while infusing a charge of said local anesthetic into the abdomen of the patient through each one of said pair of delivery needles;

advancing one of said pair of delivery sheaths over each one of said pair of delivery needles such that each one of said pair of delivery needles is received within a delivery sheath passageway and such that said delivery sheaths are situated along said delivery path;

introducing said tape into the body of the patient via the vagina and attaching each respective end of said tape to one of said delivery needles via said attachment means;

withdrawing each one of said pair of delivery needles from the abdomen of the patient through a respective delivery sheath passageway and thereby conducting each end of said tape through a respective delivery sheath such that said tape is positioned along said delivery path on opposite sides of the urethra;

detaching each respective end of said tape from a respective one of said pair of delivery needles; and withdrawing each one of said pair of delivery sheaths from the abdomen of the patient.

* * * * *